(12) United States Patent
Garbo

(10) Patent No.: US 9,681,927 B2
(45) Date of Patent: Jun. 20, 2017

(54) DENTAL CLEANING TOOL AND METHOD

(71) Applicant: Joe Garbo, Houston, TX (US)

(72) Inventor: Joe Garbo, Houston, TX (US)

( * ) Notice: Subject to any disclaimer, the term of this patent is extended or adjusted under 35 U.S.C. 154(b) by 93 days.

(21) Appl. No.: 14/710,665

(22) Filed: May 13, 2015

(65) Prior Publication Data

US 2016/0331490 A1  Nov. 17, 2016

(51) Int. Cl.
- *A61C 15/00* (2006.01)
- *A61C 3/00* (2006.01)
- *A61C 15/02* (2006.01)

(52) U.S. Cl.
CPC .............. *A61C 3/00* (2013.01); *A61C 15/02* (2013.01)

(58) Field of Classification Search
CPC ............ A61C 15/02; A61C 3/00; A61C 17/00
See application file for complete search history.

(56) References Cited

U.S. PATENT DOCUMENTS

| | | | | |
|---|---|---|---|---|
| 4,449,934 A * | 5/1984 | Salam | ................... | A61C 17/00 132/309 |
| 4,911,187 A * | 3/1990 | Castillo | ................... | A46B 7/04 132/321 |
| 5,253,661 A * | 10/1993 | Alonzo | ................... | A61C 15/00 132/321 |
| 5,538,023 A | 7/1996 | Oczkowski et al. | | |
| 6,082,999 A * | 7/2000 | Tcherny | ................... | A46B 9/04 132/308 |
| 6,085,761 A * | 7/2000 | Inaba | ................... | A61C 15/02 132/329 |
| 6,158,444 A * | 12/2000 | Weihrauch | ................... | A61C 15/02 132/200 |
| 7,997,287 B2 | 8/2011 | Jansheski et al. | | |
| 8,631,808 B1 * | 1/2014 | Weinstat | ................... | A61C 15/02 132/321 |
| 8,695,611 B2 * | 4/2014 | Snedden | ................... | A46B 9/005 132/309 |
| 9,173,479 B2 * | 11/2015 | Butz | ................... | A46B 9/005 |
| 2006/0048790 A1 * | 3/2006 | Petner | ................... | A46B 11/002 132/309 |
| 2008/0076089 A1 * | 3/2008 | Vu | ................... | A61C 3/00 433/143 |

* cited by examiner

*Primary Examiner* — Glenn Richman

(57) ABSTRACT

A dental tool having a handle with a first and second end, the first end having a cross sectional shape of a first side being half tetrahedral with rounded concave scoops terminating in a blade, the blade having an upturned point on the first side of said end and a brush on the first end. The brush may be extended from the end of said blade or positioned on the upper ridge of the tetrahedral side. The first end may have opposing tetrahedral sides with brushes along the central ridge defining the tetrahedral side. The opposite end of the tool may have a spoon shaped extension that is angled.

17 Claims, 4 Drawing Sheets

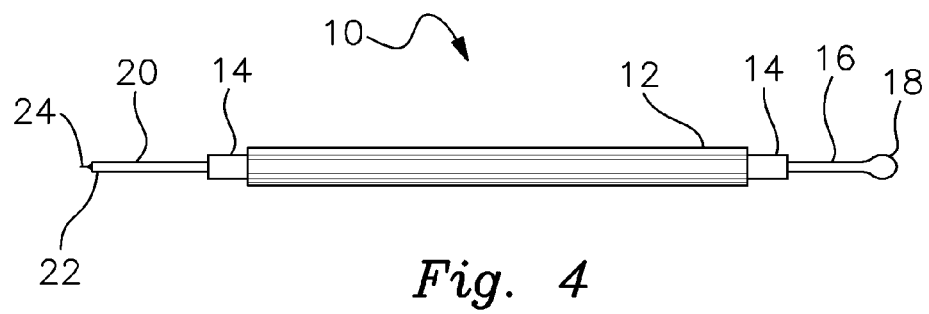
Fig. 4
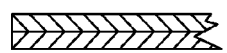 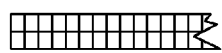 
Fig. 5A   Fig. 5B   Fig. 5C
  
Fig. 6A   Fig. 6B   Fig. 6C
 
Fig. 7A   Fig. 7B

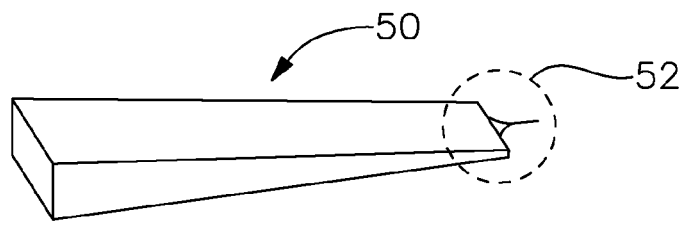 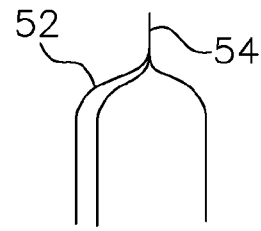
Fig. 8A  Fig. 8B
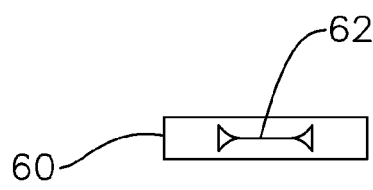 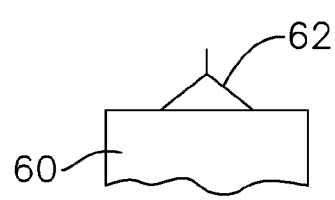
Fig. 9A  Fig. 9B
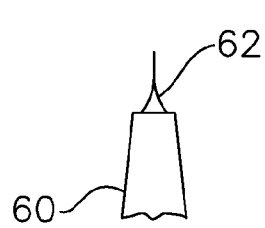 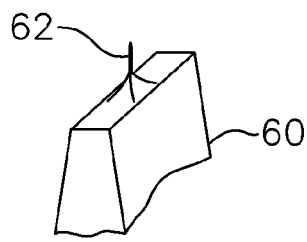
Fig. 9C  Fig. 9D
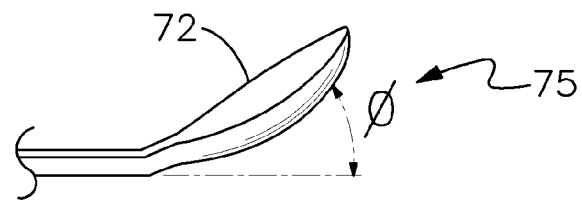
Fig. 10

DENTAL CLEANING TOOL AND METHOD

BACKGROUND OF THE INVENTION

Field of the Invention

This invention relates to dental tools, and more particularly to an improved Dental Cleaning Tool and Method.

CROSS REFERENCE TO RELATED APPLICATIONS

Not applicable

DESCRIPTION OF RELATED ART

Various prior art devices are used to clean plaque and tartar from teeth. Toothbrushes are a traditional device used by individuals. Dental practitioners have different pointed tools with various end configurations that are used to remove plaque from teeth. In some cases, the dental tool has a sharp pointed end for picking between teeth. In other prior art, the tool may have a flat paddle-like structure for scraping the teeth.

None of the prior art teaches or suggest the innovative methods and apparatus described herein. The present invention results in a dental tool with two ends, one having a combination sharp edged point and scoops and brush extending there from or between the scoops, and the other end having a cup-like protrusion.

SUMMARY OF THE INVENTION

In accordance with another preferred embodiment of the invention there is disclosed a dental tool having a handle with a first and second end, the first end having a cross sectional shape of a first side being half tetrahedral terminating in a blade, the blade having an upturned point on the first side of the end, and one or more brushes on the first end.

In accordance with another preferred embodiment of the invention there is disclosed a dental tool having a handle, the handle with a first end with a half tetrahedral side, the tetrahedral side having concave surfaces on each of the half tetrahedral side, the end terminating at a flattened blade, and the blade having a brush extended on the upper central ridge of the tetrahedral side behind the end of the blade.

In accordance with yet another preferred embodiment of the invention there is disclosed a dental tool having a handle with a first and second end, the first end having a cross sectional shape of a first side being half tetrahedral scoops connected by a central ridge, a blade having an upturned point on the first side of the end, a brush on the first end, the second end having a spoon shaped extension.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 4 is a side view of a handle having two ends for a dental tool according to a preferred embodiment of the invention.

FIGS. 5A, B and C are side views of the central portion of a handle of a dental tool according to a preferred embodiment of the invention.

FIGS. 6A, B, and C are cross sectional views of a handle of a dental tool according to a preferred embodiment of the invention.

FIGS. 7A and B are perspective views of an end of a handle for a dental tool according to a preferred embodiment of the invention.

FIGS. 8A and B are perspective views of an end of a dental tool according to a preferred embodiment of the invention.

FIGS. 9A, B, C and D is a plan, side elevation, end elevation and perspective view, respectively of an end of a handle of a dental tool according to a preferred embodiment of the invention.

FIG. 10 is a side perspective view of an end of a handle of a dental tool according to a preferred embodiment of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the issued claims and as a representative basis for teaching one skilled in the art to employ the present invention in virtually any appropriately detailed system, structure or manner.

Figure 1:
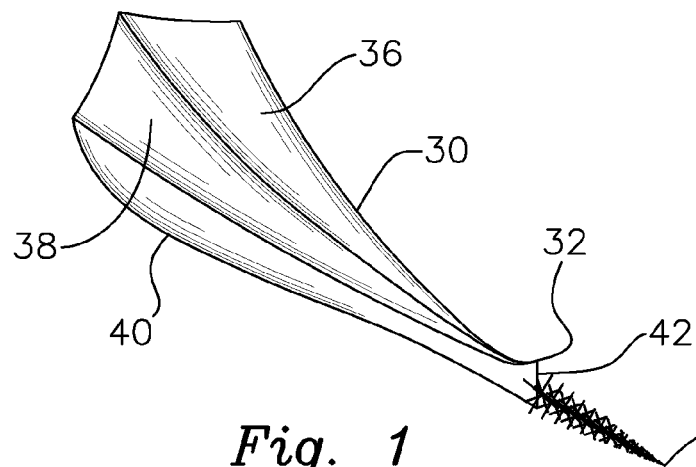
FIG. 1 is a perspective view of one end of a dental tool according to a preferred embodiment of the invention.

Turning now to FIG. 1, there is shown a pick 32 and brush 34 formed on a shaft 30 that may be placed at the end of a handle as further shown and described in FIG. 4. The shaft 30 is shown with one side having two opposing scoops 36 and 38 that narrow and come to a point at pick 32. Pick 32 preferably is sized to fit between the gap in teeth to facilitate removal of plaque or tartar that forms on the teeth and in the crevices between teeth. As plaque or tartar is scraped off a tooth, it may collect on the scoops 36 or 38 for later removal. Scoops 36 and 38 are formed in a half tetrahedral separated by a central ridge.

Brush 34 is an extension of blade 42 that is formed at the conjunction of scoops 36 and 38 and bottom 40. Pick 32 has a sharp end that is upturned to help in scraping and pulling plaque or tartar from between the teeth. Brush 34 is formed at the end of blade 43 and fits between teeth to further help in the removal of plaque that has been scraped or dislodged by pick 32.

Figure 2:
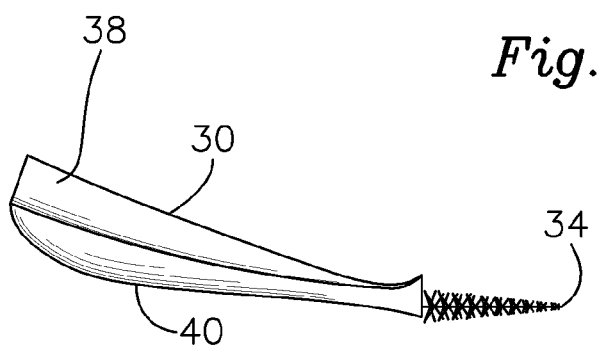
FIG. 2 is a side perspective view of a dental tool according to a preferred embodiment of the invention.

In operation, pick 32 may be used both on the front surface of teeth or on the back surface to remove plaque and collect it in concave scoops 36 and 38. Brush 34 further enhances the removal of dislodged or loose plaque, tartar or other debris. FIG. 2 shows in side view of shaft 30 with pick 32 and brush 34 extended therefrom. Shaft 30, pick 32, and brush 34 may all be manufactured in any of a variety of materials including plastic, stainless steel, or other composites. Brush 34 may be cut or machined integrally with the shaft 30 or be appended as a separate item after manufacture of pick 32, concave scoops 36 and 38, bottom 40 and blade 42.

Figure 3:
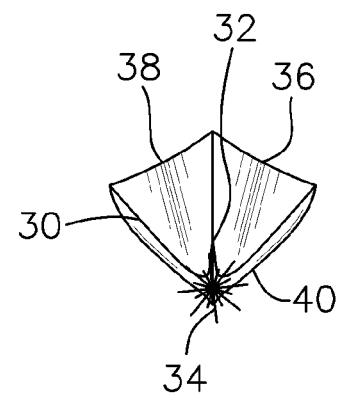
FIG. 3 is an end view of a dental tool according to a preferred embodiment of the invention.

FIG. 3 shows shaft 30 in end plan view with scoops 36 and 38 and pick 32 at the end of shaft 30. Brush 34 is shown extended from the blade of pick 32 with bottom rounded portion 40 on the opposite side of tetrahedral side formed by scoops 36 and 38.

FIG. 4 shows a two ended handle 10 with needle 24 connected to end 22, mounted on tube 20, connected to hub 14 and handle center 12. On the opposite side of needle 24 is positioned second hub 14, tube 16 terminating in spoon 18. As is readily apparent, shaft 30 of FIGS. 1 through 3 may be attached to tube 20 to become part of the two ended handle 10. Two ended handle 10 provides a convenient and ergonomic way to manipulate each end of the handle in the mouth for dental care. Spoon 18 is further described below in FIGS. 7A and 7B.

Handle Center 12 may be smooth or configured with a variety of textures for easy grip. FIG. 5A shows a herringbone patter, FIG. 5B shows a checkerboard pattern, and FIG. 5C shows concentric ring grips. Other gripping patterns well known in the art may be employed as well as an additional wrap of rubber or other tacky material. FIGS. 6A, B and C show in cross sectional view handle center 12 in a variety of configurations including octagonal in FIG. 6A, hexagonal in FIG. 6B, and circular in FIG. 6C. Again, any of a variety of cross sectional shapes may be employed and still be within the spirit of the invention.

FIG. 7A shows spoon 18 as an extended spoon shape with elongated concavity. Spoon 19, an alternative design, shows an extended spoon with a generally circular and deeper concavity than spoon 18. Each is designed as one mechanism for scraping and removal of plaque or tartar from the teeth. By using a spoon, the user may reach around the edges of each tooth and cup the tooth closely in such a way as to scrape and remove debris. The spoon also permits reaching behind the teeth for removal.

FIGS. 8A and 8B shows an alternative pointed end to the dental tool of the present invention. Wedge 50 terminates with needle extension 52 for insertion between teeth of the end portion of wedge 50. Needle extension 52 as shown close up in FIG. 8B has a pointed end 54 that serves as a kind of toothpick to go between the teeth and dislodge debris. Needle extension 52 is configured to be of a size that can fit between the gaps in teeth and scrape away plaque or tarter between the teeth.

FIGS. 9A through 9D show an alternative extension of shaft 60. FIG. 9A is a plan view of extension 62, with FIG. 9B showing an elevation view that depicts a pointed needle end of extension 62. FIG. 9C shows a side view of extension 62, whereas FIG. 9D shows a perspective view of extension 62. As is readily apparent, extension 62 is configured to provide access to the spaces between teeth for scraping and removing debris.

FIG. 10 shows an end of a dental too with scoop 72 angled at angle theta 75. Theta 75 may be of any of a variety of angles to facilitate reaching behind the teeth for removal of debris. Preferably angle theta 75 should be approximately 30-35 degrees.

Figure 11:
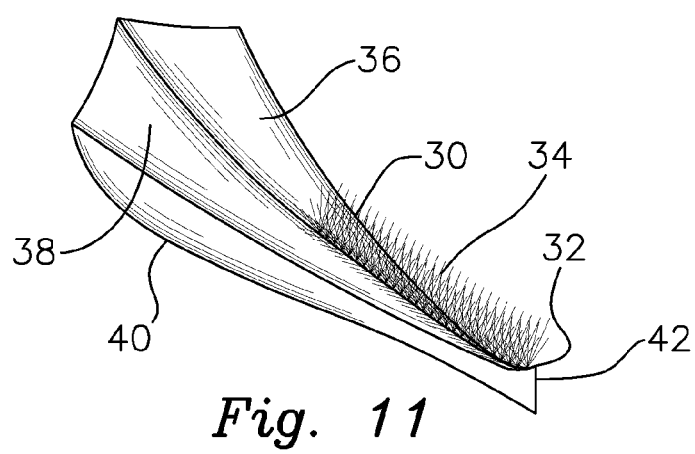
FIG. 11 is a perspective view of an angled end of a dental tool according to a preferred embodiment of the invention.

FIG. 11 shows dental tool similar to FIG. 1 having a pick 32 formed on a shaft 30 that may be placed at the end of a handle as further shown and described in FIG. 4. The shaft is shown with one side having two opposing scoops 36 and 38 that narrow and come to a point at pick 32. Pick 32 preferably is sized to fit between the gap in teeth to facilitate removal of plaque or tartar that forms on the teeth and in the crevices between teeth. As plaque or tartar is scraped off a tooth, it may collect on the scoops 36 or 38 for later removal. FIG. 11 as an alternative embodiment has brush 34 positioned on the ridge connecting scoops 36 and 38, positioned just behind pick 32. While blade 42 is pushed between teeth, brush 34 acts to dislodge and remove debris along its length.

Figure 12:
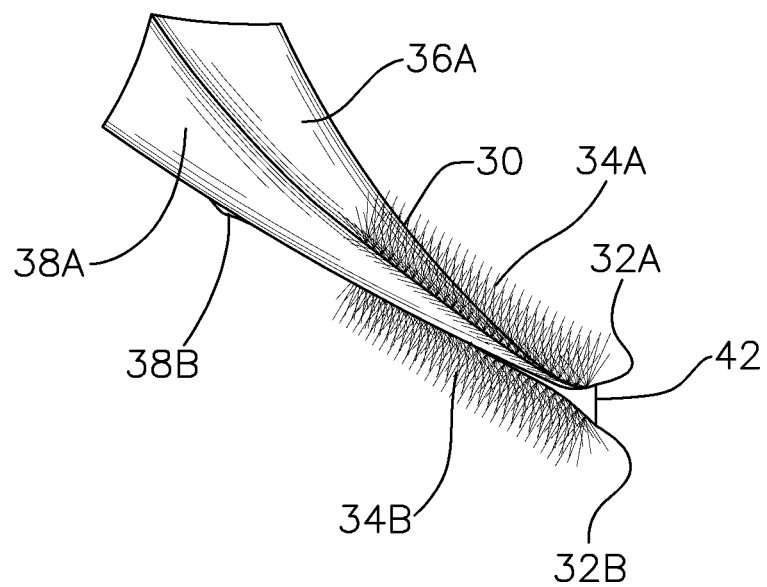
FIG. 12 is a perspective view of an angled end of dental tool according to another preferred embodiment of the invention.

FIG. 12 shows a dental tool similar to FIG. 11 having two opposite sides with scoops 36A and 38A, and opposite side having scoop 38B next to reciprocal scoop to 36A not shown. Picks 32A and 32B are on each end of blade 42 formed at the end of shaft 30. Shaft 30 is shown with two opposing scoops 36A and 38B that narrow and come to a point at pick 32. On the opposite side, are mirror images of scoops 36A and 38A. As plaque or tartar is scraped off a tooth, it may collect on the any of the scoops for later removal. FIG. 12 has upper brush 34A positioned on the ridge connecting scoops 36A and 38A, positioned just behind pick 32A. On the bottom side of shaft 30, brush 34B is similarly positioned between the two scoops positioned just behind pick 32B. In one embodiment, the cross sectional shape of the opposing tetrahedral sides would resemble a 4-sided diamond shape with curved inward sides.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the issued claims.

I claim:

1. A dental tool handle comprising:
   a handle having a central generally cylindrical portion, and a first and second end;
   said first end having a cross sectional shape of a first side being half tetrahedral terminating in a blade positioned on the tetrahedral portion of the first side;
   said blade having an upturned point on said tetrahedral portion of said first side of said end.

2. The dental tool of claim 1 further comprising a brush extended from said blade.

3. The dental tool of claim 1 further comprising a brush positioned on the center of said tetrahedral first side.

4. The dental tool of claim 1 further comprising an extended pick on said tetrahedral first side on the top edge of said blade.

5. The dental tool of claim 1 further comprising a handles having a cross sectional dimension of any one of the following shapes: round, hexagonal, or octagonal.

6. A dental tool comprising:
   a handle having a first and second end connected by a central portion;
   a point on said first end;
   said second end having an upturned shaft extended from the handle terminating in a generally concave extension wherein said shaft is angled between approximately 15 and 60 degrees.

7. The dental tool as claimed in claim 6 further comprising a brush is extended from the end of said first end.

8. The dental tool as claimed in claim 7 wherein said brush is extended around the first end of the handle.

9. The dental tool as claimed in claim 6 wherein said concave extension is spoon-shaped.

10. The dental tool as claimed in claim 6 wherein said concave extension is generally oblong shaped.

11. A dental tool comprising:
a handle having a first and second end, the handle having ridges around a portion of said handle;
said first end having a cross sectional shape of a first side being half tetrahedral scoops connected by a central ridge;
a blade having an upturned point on said first side of said end;
a brush on said first end; and
said second end having a spoon shaped extension.

12. The dental tool of claim 11 wherein said spoon shaped extension is angled upward at an angle of approximately 45 degrees.

13. The dental tool of claim 11 wherein said handle has an opposing half tetrahedral side to said first tetrahedral side.

14. The dental tool of claim 11 wherein said handle has a cross sectional shape of one of the following: circle, hexagon, octagon.

15. The dental tool of claim 11 wherein said spoon shaped extension is angled between 15 and 30 degrees.

16. The dental tool of claim 11 further comprising an extended toothpick shaped end opposite the end having a blade.

17. The dental tool as claimed in claim 11 wherein said ridges are in a pattern from the following: parallel, herringbone or rectilinear.

* * * * *